United States Patent [19]

Hildebrand et al.

[11] Patent Number: 5,017,386

[45] Date of Patent: May 21, 1991

[54] METHOD OF REDUCING ODOR ASSOCIATED WITH HEXANAL PRODUCTION IN PLANT PRODUCTS

[75] Inventors: David F. Hildebrand; Thomas R. Kemp; Roger Andersen, all of Lexington; John H. Loughrin, Alton, all of Ky.

[73] Assignee: University of Kentucky Research Foundation, Lexington, Ky.

[21] Appl. No.: 416,674

[22] Filed: Oct. 5, 1989

[51] Int. Cl.[5] .......................... A21D 2/00; A21D 8/02; A23L 1/10

[52] U.S. Cl. ....................................... 426/18; 426/31; 426/46

[58] Field of Search ............................ 426/18, 31, 46

[56] References Cited

U.S. PATENT DOCUMENTS

| | | | |
|---|---|---|---|
| 3,048,492 | 8/1962 | Barton | 99/140 |
| 3,585,047 | 6/1971 | Fujimaki et al. | 99/98 |
| 3,718,479 | 2/1973 | Kanno et al. | 99/17 |
| 4,232,044 | 11/1980 | Chiba et al. | 426/44 |
| 4,642,236 | 2/1987 | Friend et al. | 426/44 |
| 4,677,247 | 6/1987 | Kitamura | 800/1 |
| 4,769,243 | 9/1988 | Kanisawa et al. | 426/33 |

FOREIGN PATENT DOCUMENTS

| | | |
|---|---|---|
| 137965 | 6/1978 | Japan . |
| 033447 | 10/1978 | Japan . |
| 154721 | 3/1985 | Japan . |
| 270701 | 6/1987 | Japan . |
| 052815 | 9/1988 | Japan . |

OTHER PUBLICATIONS

Wang and Hildebrand, "Biosynthesis and Regulation of Linolenic Acid in Higher Plants", Plant Physiol Biochem (1988).
Schewe et al., "Enzymology and Physiology of Riticulocyte etc", (1986).
Hatanaka et al., "Biosynthetic Pathway for C-Aldehydes Formation from Linolenic Acid in Green Leaves", (1987).
Vick & Zimmerman, "Oxidative Systems for Modification of Fatty Acids: The Lipoxygenase Pathway" (1987a).
Vick & Zimmerman, "Pathways of Fatty Acid Hydroperoxide Metabolism in Spinach Leaf Chloroplasts", (1987b).
Mack et al., "Lipoxygenase Isozymes in Higher Plants: Biochemical Properties & Physiological Role", (1987).
Rackis et al., "Flavor Problems of Vegetable Food Proteins", (1979).
Arai et al., "N-Hexanal and Some Volatile Alcohols etc", (1970).
Wolf, "Lipoxygenase and Flavor of Soybean Protein Productsp", (1975).
Axelrod et al., "Lipoxygenase from Soybeans", (1981).
Buttery et al., "Characterization of Some Volatile Constituents of Bell Peppers", (1969).
Matoba et al., "Lipoxygenase-2 Isozyme is Responsible for Generation of N-Hexanal in Soybean Homogenate", (1985).
Hildebrand & Hymowitz, "Two Soybean Genotypes Lacking Lipoxygenase-1", (1981).
Davies & Nielsen, "Genetic Analysis of a Null-Allele for Lipoxygenase-2 in Soybean", (1986).

Primary Examiner—Donald E. Czaja
Assistant Examiner—Leslie Wood
Attorney, Agent, or Firm—Lowe, Price, LeBlanc, Becker & Shur

[57] ABSTRACT

A method of reducing the formation of hexanal by plant parts comprises breaking the plant parts, adding thereto an agent comprising lipoxygenase 3 enzyme and allowing the plant parts to remain in contact with the enzyme under conditions effective to attain the desired effect. A method of producing a low odor plant part meal or flour comprises breaking up the plant parts, adding an agent with lipoxygenase 3 enzyme and allowing the plant parts to remain in contact with the enzyme under conditions effective to attain the desired effect. An improved composition comprises a hexanal producing plant part meal or flour and an agent with lipoxygenase 3 enzyme which is substantially devoid of lipoxygenase enzyme 1 and 2 activities, optionally with other edible ingredients such as other low-hexanal producing flours. Improved edible products are produced using the invention which have less objectionable odor and flavor. This invention facilitates better tailoring of the flavor of food products to the desires of the consumers.

20 Claims, 3 Drawing Sheets

METHOD OF REDUCING ODOR ASSOCIATED WITH HEXANAL PRODUCTION IN PLANT PRODUCTS

TECHNICAL FIELD

This invention relates to the field of food production and it provides a method of reducing undesirable odor and flavor associated with the formation of hexanal by plant products such as soybeans, wheat germ and the like. The plant products obtained in accordance with the invention have less odor from hexanal and can be utilized more readily by the food industry, by themselves or, in admixture with other products and/or flours.

BACKGROUND ART

Soybeans and other plant parts contain large amounts of lipoxygenases which accelerate the oxidation of unsaturated fatty acids contained therein. The term lipoxygenase (linoleate:oxygen oxidoreductase, EC 1,13,11,12), also known as lipoxidase and carotene oxidase, refers to a class of dioxygenases that catalyze the peroxidation of molecules containing cis,cis-1,4-pentadiene moieties. Lipoxygenases (LOXs) are essentially ubiquitous among eukaryotic organisms and have been demonstrated to exist in many tissues of numerous higher plants and animals. Multiple LOX forms or isozymes are often present in tissues. For example, soybean seeds contain at least three LOX isozymes which are encoded by distinct genes. These genes have been cloned and sequenced. They have regions of high homology. A LOX gene cloned from human leukocytes suggests a common evolutionary origin of plant and animal LOXs (see, Hildebrand et al. 1988 and references therein).

The principal substrates for LOXs in higher plants are linoleic acid (18C long and 2 double bonds, 1 of which is positioned 6C in from the terminal (methyl) or omega (omega)end=C18:2,omega 6) and α-linolenic acid (C18:3,omega 3). These are the terminal fatty acids synthesized in most plant tissues. The first principal fatty acid produced in fatty acid biosynthesis is palmitic acid (C16:0) which can be elongated to stearic acid (C18:0), which can be desaturated to oleic acid (C18:1). In plants, fatty acid biosynthesis up to oleic acid occurs in the plastids. Subsequent desaturation of oleic acid to linoleic and linolenic acid can occur in the chloroplasts as well as the endoplasmic reticulum (Wang and Hildebrand, "Biosynthesis and Regulation of Linolenic Acid in Higher Plants", Plant Physiol. Biochem. 26 (1988)). Linolenic acid is the most abundant fatty acid in most plant tissues whereas linoleic acid is often the most abundant fatty acid in plant seeds. Linoleic acid is the precursor of other omega 6 fatty acids such as gamma-linolenic acid (6,9,12 all cis C18:3,omega 6) and arachidonic acid (C20:4) and α-linolenic acid is the precursor of other omega 3 fatty acids such as eicosapentaenoic (C20:5) and docosahexaenoic (C22:6) acids (all of which are substrates for LOX) in the food chain.

Much of the interest in LOX is due to the importance of this enzyme in the post-harvest physiology of many food products. For many seeds with high levels of LOX and linoleic acid such as soybean seeds, the production of hexanal represents a particular problem. Hexanal, even when present in foods in very low concentrations (e.g., 5 ppb), has highly undesirable odor and flavor creating great difficulties in the production of acceptable food products containing for example, soybean homogenates. Additionally, the destruction of LOX activity is thought to be one of the principal reasons for the need for blanching of food products prior to freezing. LOX is also thought to be important in the formation of the flavor components of many fruits and vegetables including cucumbers, tomatoes, melons, etc.

Four major enzyme systems are operative in higher plants by which fatty acids are oxidatively modified: α-oxidation, β-oxidation, omega-oxidation and the LOX pathway. LOX catalyzes the peroxidative modification of polyunsaturated fatty acids which leads to the formation of various secondary lipid oxidation. This is shown in the reaction scheme set forth in FIG. 3.

The lipoxygenase (LOX) pathway can be summarized as follows. The initial event is thought to be the release of free fatty acids by lipases, but it is not known that this is always necessary. Linoleic and linolenic acids (shown in FIG. 3) are the principal substrates for LOX. The first step of the LOX-catalyzed reaction is the stereospecific removal of hydrogen from the C11 methylene group (step 1). Removal of the 11-pro-S-hydrogen results in a rearrangement to form a free radical at C13 (step 2) and LOX is reduced to the $Fe^{2+}$ form. Under aerobic conditions, the LOX-fatty acid radical complex subsequently reacts with $O_2$ forming a fatty acid peroxy radical (step 3). However, step 3 cannot take place under anaerobic conditions and thus the fatty acid radical is released from the LOX enzyme and alternative reactions occur for some LOX isozymes (see text) (step 3a) at least for the linoleoyl radical and presumably for the linolenyl radical. The fatty acid radicals (formed after steps 1 and 2) and peroxy fatty acid radicals (formed at step 3) are normally bound to the LOX enzyme (intermediates bound to the LOX enzyme are enclosed in brackets). The final step of the LOX-catalyzed reaction is the reduction of the fatty acid peroxy radical to a hydroperoxide and the oxidation of LOX back to the $Fe^{3+}$ form and release of the fatty acid product from the enzyme (step 4). The fatty acid hydroperoxides are subsequently metabolized by hydroperoxide lyase to C-6 and C-12 products (step 5) (or C-9 products with some other LOX/lyase systems) or by hydroperoxide dehydrase at least in the case of hydroperoxy-linolenic acid) to 12-oxo-cis, cis-10, 15-phytodienoic acid (12-oxo-PDA) which can be converted ultimately into jasmonic acid.

The initial event in the LOX pathway is thought to be release of free fatty acids from glycerolipids (the vast bulk of fatty acids in living cells is esterified in glycerolipids). However, some LOXs such as the reticulocyte LOX can directly attack phospholipids and even biological membranes (Schewe et al., "Enzymol and Physiology of Reticulocyte Lipoxygenase: comparison with other lipoxygenase", Adv. Enzymol. Related Areas Mol. Bio. 58: 191–272 (1986)).

Typical LOXs contain 1 mol of non-heme iron per mol of enzyme. LOX must be in the oxidized or $Fe^{3+}$ form for LOX catalyzed oxidations to proceed. LOX can be activated or oxidized by its own lipid hydroperoxide product (which at high concentrations can also cause the eventual destruction of LOX activity). LOX-$Fe^{3+}$ usually binds to either C18:2 or C18:3 in the case of higher plants and catalyzes the stereospecific removal of hydrogen from the C11 methylene group (FIG. 3). Removal of the 11-pro-S-hydrogen and subsequent rearrangement leads to the formation of the C13 radical as shown for soybean LOX-1 (FIG. 3) and LOX is reduced to the $Fe^{2+}$ form. Removal of the 11-pro-R-hydrogen, which can occur with soybean LOX 2 and 3 and other LOXs, however, results in the rearrangement of the free radical to the C-9 position (not shown).

Usually the LOX-fatty acid radical complex subsequently reacts with $O_2$ forming a lipid peroxy radical (see, FIG. 3). However, step 3 cannot take place under anaerobic conditions. Alternative reactions, therefore, take place in the case of many LOXs such as soybean LOX-1 releasing fatty acid radicals from the enzyme (FIG. 3). This reaction occurs with the linoleic acid radical and is presumed to occur with the linolenic acid radical. This leads to the so-called lipo-hydroperoxidase reactions of LOXs yielding fatty acid dimers and oxodienoic acids. For some LOXs, however, such as soybean LOX-3 and a pea LOX, reaction 3a tends to occur aerobically and the fatty acid radicals are released from the LOX enzyme and in this case can react with $O_2$ yielding peroxy radicals. These peroxy radicals are thought to be responsible for the co-oxidation reactions such as the oxidation of carotenoids and chlorophylls (Schewe et al., (1986)).

The final step of the primary LOX reactions is the reduction of the fatty acid hydroperoxy radical to a hydroperoxide (e.g., 13-(S)-hydroperoxy-9-cis-11-trans-octadecadienoic acid) and the oxidation of LOX back to the $Fe^{3+}$ form and release of the fatty acid product from the enzyme (see, FIG. 3, step 4). Hydrogen abstraction is the rate-limiting step of the overall reaction. The decisive feature of all LOX-catalyzed reactions in both plants and animals is the homolytic cleavage of a sigma bond (e.g., C-H) with the formation of intermediate radicals.

The fatty acid hydroperoxides resulting from LOX action are metabolized by one of two major pathways operative in higher plant tissues. In one pathway, hydroperoxide lyase catalyzes the cleavage of 13-hydroperoxy linoleic or linolenic acid into the 12 carbon compound, 12-oxo-9-dodecenoic acid, and the 6 carbon aldehydes, hexanal or cis-3-hexenal (see, FIG. 3 step 5). Nine carbon oxo fatty acids and aldehydes are formed from the 9-hydroperoxy fatty acids. The 12-oxo-cis-9-dodecenoic acid and cis-3-hexenal undergo isomerization to the more stable 12-oxo-trans-10-dodecenoic acid and trans-2-hexenal (see, FIG. 3) (Hatanaka et al., Chem. Phys. Lipids 44: 341–361 (1987); Vick and Zimmerman, "Oxidative Systems for Modification of Fatty Acids: the Lipoxygenase Pathway"-in The Biochem. of Plants: A Comprehensive Treatise, Stumpf. Ed., Vol. 9, pp 53–90, Academic Press, Orlando, Fla. (1987a)). Hexanal and hexenals are often converted to their corresponding alcohols by alcohol dehydrogenase. cis-3-Hexen-1-ol and trans-2-hexenal are known as leaf alcohol and aldehyde and are associated with the "green odor" of leaves as is characteristic for freshly cut grass. The 12-oxo-trans-10-dodecenoic acid, known as wound hormone or traumatin, is readily oxidized non-enzymatically to trans-2-dodecenedioic acid, commonly known as traumatic acid.

The second pathway for metabolism of hydroperoxy fatty acids (at least for linolenic acid) in plants is the conversion into an allene oxide by hydroperoxide dehydrase (Vick and Zimmerman (1987a), supra). The allene oxide can undergo hydrolysis resulting in the formation of ketols. Alternatively, the allene oxide can undergo rearrangement and cyclization resulting in the formation of 12-oxo-cis,cis-10,15-phytodienoic acid (12-oxo-PDA). The 12-oxo-PDA can be converted by a series of reactions into jasmonic acid (Vick and Zimmerman 1987a, supra; Vick and Zimmerman, Plant Physiol. 85: 1073–1078 (1987) (Vick and Zimmerman (1987b))).

In spite of the rapid increase in information concerning the role of LOX in mammalian physiology and of the fairly extensive biochemical and genetic studies that have been done with plant LOXs, little definitive information is available concerning physiological roles for plant LOXs. (Mack et al., Current Topics Biol. Med. Res. 13: 127–154 (1987); Vick and Zimmerman (1987a), supra, and Hildebrand et al. (1988), supra, recently presented reviews on this subject).

Hexanal is a volatile aldehyde formed from soybean seeds during processing. This compound has an undesirable aroma which has limited the widespread use of soybean proteins in food products (Rackis, J. J., Sessa, D. J. & Honig, D. H., J. Amer. Oil Chem. Soc. 56: 262–271 (1979)). Lipoxygenases (linoleate: oxygen oxidoreductase, EC 1.13.11.12) which are thought to be key enzymes responsible for hexanal formation, exist in soybean seeds as three distinct isozymes (Arai, S., et al. Agr. Biol. Chem. 34: 1420–1423 (1970); Wolf, W. J. J. Agr. Food Chem. 23: 136–140 (1975); Axelrod, B., Cheesbrough, T. M. & Laakso, S. Methods Enzymol. 71: 441–451 (1981)).

It was thought that all three lipoxygenase isozymes contribute to hexanal production, with lipoxygenase isozyme 2 being the most effective (Rackis, J. J., Sessa, D. J. & Honig, D. H. J. Amer. Oil Chem. Soc. 56: 262–271 (1979); Arai, S., et al. Agr. Biol. Chem. 34: 1420–1423 (1970); Wolf, W. J. J. Agr. Food Chem. 23: 136–140 (1975); Buttery, R. G., et al. J. Ag. Food Chem. 17: 1322–1327 (1969); Hatanaka, A., Kajiwara, T. & Sekiya, J. Chem. Phys. Lipids 44: 341–361 (1987); Matoba, T. et al. J. Agric. Food Chem. 33: 852–855 (1985)).

Hexanal is a potent odor and flavor compound with a very low olfactory threshold (Buttery, R. G., et al. J. Ag. Food Chem. 17: 1322–1327 (1969)) which makes it undesirable in many food products. It is thought to be formed by hydroperoxidation of linoleic acid (cis,cis-9,12-octadecadienoic acid) in plant tissues through the action of lipoxygenase and subsequent cleavage of the product by hydroperoxide lyase (Hatanaka, A., Kajiwara, T. & Sekya, J. Chem. Phys. Lipids 44: 341–361 (1987)). Soybean (Glycine max L. Merr.) seeds and other plant parts contain relatively high levels of both linoleate and lipoxygenase and high levels of hexanal are produced from aqueous homogenates of soybean seeds (Rackis, J. J., Sessa, D. J. & Honig, D. H. J. Amer. Oil Chem. Soc. 56: 262–271 (1979); Arai, S., et al. Agr. Biol. Chem. 34: 1420–1423 (1970); Wolf, W. J. J. Agr. Food Chem. 23: 136–140 (1975); Axelrod, B., Cheesbrough, T. M. & Laakso, S. Meth. Enzymol. 71: 441–451 (1981)). This has limited the use of whole soybeans and soybean protein as well as other products in many foods.

Soybeans have been screened for mutants missing seed lipoxygenase(s). Mutants with nondetectable or very low lipoxygenase activity were found for all three known soybean seed lipoxygenase isozymes (Hildebrand, D. F. & Hymowitz, T. J. Amer. Oil Chem. Soc. 58: 583–586 (1981); Kitamura, K. J. Agric. Biol. Chem. 48: 2339–2343 (1984)). The null mutants were inherited as simple recessive alleles. Lipoxygenases 1 and 2 were tightly linked but lipoxygenase 3 was inherited independently of lipoxygenases 1 and 2 (Davies, C.

S. & Nielsen, N. C. Crop Sci. 26: 460–463 (1986)). Davies and Nielsen (Davies, C. S. & Nielsen, N. C. Crop Sci. 27: 370–371 (1987)) developed near-isogenic lines backcrossed to the soybean cultivar "Century" that are homozygous for one or two of the lipoxygenase null alleles. No triple null lines have been found because of the tight linkage of lipoxygenase 1 and 2 and possible lethality of low frequency recombinants. Matoba et al. (Matoba, T. et al. J. Agric. Food Chem. 33, 852–855 (1985) examined the generation of hexanal by aqueous seed homogenates of the original lipoxygenase null mutants and concluded that lipoxygenase 2 is largely responsible for the generation of hexanal. Davies et al. (Davies, C. S., Nielsen, S. S. & Nielsen, N. C. J. Amer. Oil Chem. Soc. 64, 1428–1432 (1987)) also concluded that elimination of lipoxygenase 2 through genetic selection was important in the flavor improvement of soybean preparations.

Japanese Patent Application JA-137965 to Sugiyama Sangyo Kag describes the manufacture of noodles having improved texture and color with flour containing a small amount of soybean extract with lipoxidase activity. No mention is made in the abstract as to what type of lipoxygenase the activity relates to. Nor is there a mention as to a reduction in hexanal production and/or its odor or flavor.

Japanese Patent Application JA-033447 to Ajinomoto KK describes the production of a cheese-like protein food obtained by treating soybean with a mixture of enzymes to improve its taste and flavor. One of the enzymes utilized is lipase which renders a product free of bean smell. However, no description of the enzyme is made in the abstract.

Japanese Patent Application JP-052815 relates to the production of soybean protein by treating soybeans having the activities of two of the three lipoxygenase isoenzymes L-1, L-2 and L-3 simultaneously eliminated. This reference teaches away from the present invention.

Japanese Patent Application JP-170701 to Takasago Perfumery Kk relates to the preparation of a grass-flavored substance by grinding raw soybeans, adding unsaturated fatty acids, and optionally lipase enzyme, and stirring. It is said in the abstract that the yield of flavored substance can be increased by utilizing the lipase enzyme.

Japanese Patent Application JP 154721 relates to a food composition containing proteins decomposed by enzymes such as lipase. Among the foods is listed soybean juice, of which it is said that a more digestible form with high nutritive value is obtained.

U.S. Pat. No. 4,769,243 to Kanisawa et al. is related to JP-170701 discussed above and discloses a method of preparing compounds with green aroma by grinding raw soybeans in water at or below 60° C., in the presence of air or oxygen. A lipase enzyme can be optionally added or substituted for the unsaturated higher fatty acids. A stronger green aroma is said to be obtained by adding both the fatty acid and the lipase together (see column 2, lines 1–8, 51–69 of Kanisawa et al.). The patent indicates that n-hexanal is utilized in the production of green aroma (see column 1, lines 21–24 of Kanisawa).

U.S. Pat. No. 4,232,044 to Chiba et al. describes the improvement of food protein flavor by the enzymatic conversion of aldehydes and alcohols (see column 2, lines 26–42 of Chiba et al.) by utilizing an aldehyde dehydrogenase and an alcohol dehydrogenase. Also disclosed is a process for improving the flavor of protein containing aldehydes and alcohols which relies on the reaction of the protein with aldehyde dehydrogenase or aldehyde oxidase to convert aldehydes to acids (see e.g., claim 1 of the patent).

U.S. Pat. No. 3,718,479 relates to a treatment of soybeans for use in processed foods involving the addition of sulfurous acid and lactic acid bacteria, steaming and fermentation with proteolytic and macerating activity containing microorganisms, drying and pulverizing the soybeans. The process is particularly interesting because enzymes such as lipoxygenase are inactivated. This teaches away from the present invention (see column 2, lines 38–41 of Kanno et al.).

U.S. Pat. No. 3,585,047 to Fujimaki et al. relates to a process of incubating soybean curd or defatted soybean flour with proteolytic enzymes to release a beany and astringent flavor and lipid materials from the proteinaceous constituents. The process is designed for removing among others the hexanal content of the product (see column 2, lines 20–47 of Fujimaki et al.) by means of enzymes such as proteolytic enzymes.

U.S. Pat. No. 3,048,492 to Barton relates to a reduction in the flavor of leguminous food materials by treating with an oxidizing enzyme to elevate the carbonyl content thereof (see column 1, lines 16–22 of Barton). A series of leguminous foods are listed in column 2, lines 11–17 of this patent.

U.S. Pat. No. 4,642,236 to Friend et al. relates to a process for reducing undesirable flavor components in a vegetable protein material such as soybean derivatives by contacting with a mold of the genus Rhizopus or Asoerqillus. A source of the undesirable flavor is admitted to be the oxidation of native lipids contained in the soybean material. This patent attributes this undesirable flavor to the presence of lipoxygenase which can catalyze the oxidation of lipids and produce hydroperoxide compounds which can undergo further transformation by enzymatic and non-enzymatic means to yield products which also adversely affect the flavor of the soybean product. N-hexanal is mentioned as one of them (see column 2, lines 1–19 of Friend et al.)

U.S. Pat. No. 4,677,247 issued to Kitamura describes the production of odorless soybean products by breeding soybeans to produce a variety holding the homozygous recessive $lx_2$ and $lx_3$ genes which results in the lipoxygenase L-2 and L-3 lacking characteristics. Accordingly, the inventor proposes that the reduction in the level of enzyme lipoxygenase 3 will reduce the undesirable taste characterized by a grassy flavor and bitterness typical of soybean products. This is contrary to the present invention.

Accordingly, there is a need for improved plant products like soybeans and soybean flour and meal and wheat germ which have reduced amounts of undesirable odor producing ingredients. These products may be utilized in higher amounts than is currently possible with alimentary products.

DISCLOSURE OF THE INVENTION

This invention relates to a method of reducing formation of hexanal by plant parts, comprising
  breaking up of the plant parts;
  adding thereto an agent comprising lipoxygenase 3 enzyme; and
  allowing the plant parts to remain in contact with the enzyme under conditions effective to attain the desired effect.

Also part of this invention is an improved soybean composition comprising
- a plant part meal or flour; and
- an agent comprising lipoxygenase 3 enzyme, optionally substantially devoid of lipoxygenase 1 and 2 activities, said lipoxygenase 3 enzyme being present in an amount sufficient to reduce the formation of hexanal by the meal or flour.

Still part of this invention is a method of producing an improved plant part meal or flour which comprises
- breaking up parts of a plant capable of producing hexanal;
- adding thereto an agent comprising lipoxygenase 3 enzyme; and
- allowing the plant parts to remain in contact with the enzyme under conditions effective to attain the desired effect.

Another aspect of this invention relates to a composition of improved flavor, comprising
- a plant part meal or flour, said plant parts being capable of producing hexanal;
- a flour other than soybean flour; and
- an agent comprising lipoxygenase 3 enzyme, preferably substantially lacking lipoxygenase 1 and 2 enzyme activities, said lipoxygenase 3 enzyme being present in an amount sufficient to prevent formation of hexanal by the soybean.

Also part of this invention is an edible product made from a low odor composition comprising a high hexanal-producing plant flour and an agent comprising lipoxygenase 3 enzyme, substantially devoid of other lipoxygenase activities such as lipoxygenase 1 and 2.

Flavor is comprised of taste and odor. In many foods, odor is more important than taste to the flavor. For example, melon and peach both taste sweet, but the difference in their flavors is due to different odors in these two foods. A characteristic odor (aroma) is important to organoleptic appreciation of foods but certain compounds in relatively high concentrations can impart an objectionable flavor. The compounds that give rise to food odor rise in the back of the throat as we consume a food and are sensed by the olfactory epithelium of the nasal cavity.

In another aspect, this invention an edible product made from a nearly odorless composition comprising a hexanal producing plant flour, a flour other than soybean flour and an agent comprising lipoxygenase 3 enzyme substantially devoid of other lipoxygenase activities such as lipoxygenases 1 and 2.

A more complete appreciation of the invention and many of the intended advantages thereof will be readily perceived as the same becomes better understood by the reference to the following detailed description when considered with the accompanying figures.

Other objects, advantages and features of the present invention will become apparent to those skilled in the art from the following discussion.

BEST MODE FOR CARRYING OUT THE INVENTION

This invention arose from a desire by the inventors to produce better quality soybean and soybean flour as well as products such as wheat germ and the like which are high hexanal producers. Of particular importance is the disappearance of a typical unpleasant odor encountered in products obtained by prior art methods.

Contrary to what was found by the prior art, the inventors concluded that the addition lipoxygenase 3 enzyme to soybean preparations surprisingly decreased hexanal yield. This decrease was considerable, at times being as high as 1/10 to 1/20 fold, and even greater.

Figure 1:
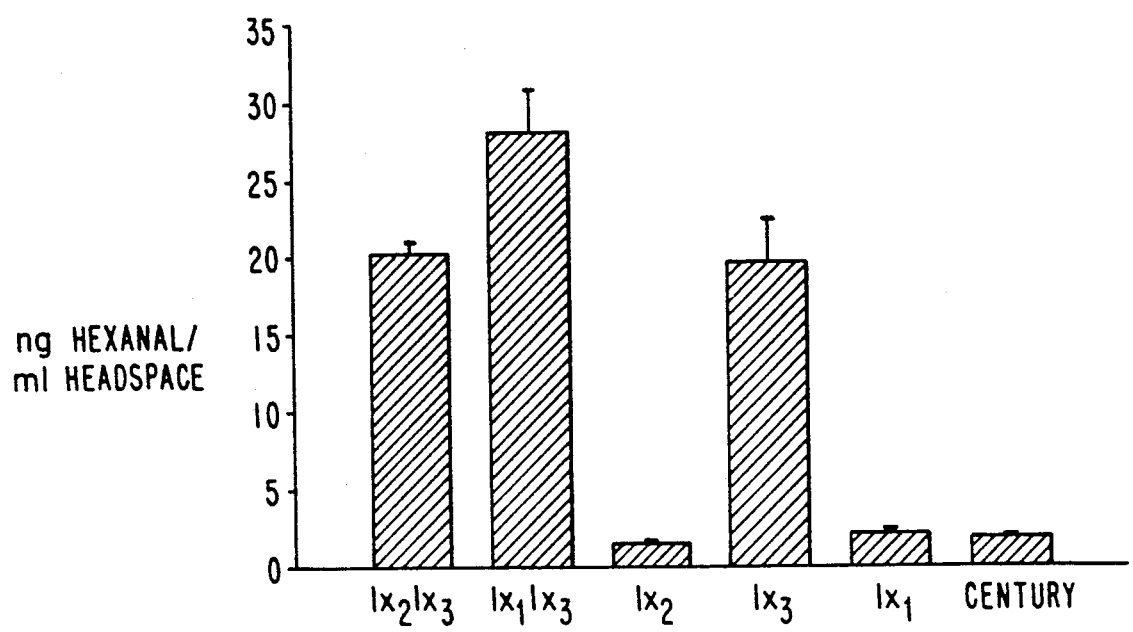
FIG. 1 shows a comparative study of the production of hexanal by aqueous homogenates of lyophilized, powdered meal from mature soybean seeds of the backcrossed mutant lines described by Davies and Nielsen (Davies C. & Nielsen, N. C. Crop Sci. 27:370–371 (1987)), and wild-type recurrent parent "Century". The genotypes designated $1x_2 1x_3$, $1x_1 1x_3$, $1x_2$, $1x_3$ and $1x_1$ are lines backcrossed to Century which are homozygous recessive for the null (or very low) alleles of lipoxygenase 2 and 3 (produce lipoxygenase 1 only), 1 and 3 (produce lipoxygenase 2 only), lipoxygenase 2 (producing lipoxygenases 1 and 3 only), lipoxygenase 3 (producing lipoxygenases 1 and 2 only), and lipoxygenase 1 (produce only lipoxygenases 2 and 3), respectively. Century's seeds contain high levels of the three lipoxygenase isozymes as do all widely grown commercial soybean cultivars.

As the prior art, the present inventors also found that lipoxygenase 2 enzyme present in soybean seeds is important and active in the formation of hexanal. This is shown in FIG. 1 attached to this application. However, subsequent to the initial lipoxygenase null backcrossed line studies, the inventors found that the major effect on hexanal reduction was in fact attributable to the presence of lipoxygenase 3 enzyme activity. This effect, the inventors concluded, was different from and contrary to the expected behavior of a lipoxygenase. The prior art in fact teaches that the lipoxygenases 1, 2 and 3 increase the odor and "grassy flavor" of soybeans (see, e.g., U.S. Pat. No. 4,677,247 to Kitamura). The lipoxygenase 3 enzyme, together with lipoxygenase 2, was, in particular, implicated by this prior art patent as responsible for the undesirable aroma of soybeans.

In the present inventors' hands, however, all lines null for lipoxygenase 3 showed a considerably higher hexanal yield than those with normal lipoxygenase 3 levels as can be seen from FIG. 1. These results were obtained in the presence or absence of added fatty acid substrates. In general, the addition of lipoxygenase 3 enzyme to, e.g., soybean preparations indicated a near linear correspondence between the amount of enzyme added and the reduction in hexanal content in the product as well as a reduction in its undesirable odor. The inventors have shown that the activity of the enzyme was responsible for the decrease in undesirable odor and production of hexanal in soybean, e.g., by autoclaving the preparations containing lipoxygenase 3 enzyme. The previously seen effect on the soybean preparations disappears upon this treatment.

This invention provides a method of reducing the formation of hexanal by plant parts, which comprises
- breaking up parts of a hexanal-producing plant;
- adding thereto an agent comprising lipoxygenase 3 enzyme; and
- allowing the plant parts to remain in contact with the enzyme under conditions effective to attain the desired effect.

The present method has particular utility in the preparation of edible food products utilizing, e.g., soybeans, soybean products, and wheat germ, among others.

In addition, the present method is also applicable to the substitution of a plant preparation, e.g., soybean or wheat germ, for other flours in mixtures thereof for the preparation of food-stuffs which prior to the present invention did not utilize soybean due to its adverse odor characteristics. Higher amounts of soybeans can be utilized than were previously possible.

In a particular aspect of the invention, the soybeans are broken, e.g., up into a powder, for processing into an edible product. The technology for the preparation of, e.g., meals or flours is known in the art and need not be further described herein.

The agent comprising the lipoxygenase 3 enzyme which is added to the soybean may be a lipoxygenase 3 agent substantially lacking lipoxygenase 1 and 2 activities. A protein preparation with high lipoxygenase 3 but little or no lipoxygenase 1 or 2 can be readily prepared on an industrial scale using a one step procedure. This can be accomplished by making a water extract of meal prepared from seeds of the lipoxygenase 2 mutant and subjecting this extract to chromatofocusing or anion-exchange chromatography. The peak of lipoxygenase 3 activity which is easily separable from lipoxygenase 1 may then be collected and used.

In another aspect of this invention, the plant parts, e.g., beans, are contacted with the lipoxygenase 3 enzyme agent at a temperature at which the enzyme is active and the plant does not decompose. The temperature range for activity of the enzyme is known in the art. Suitable is a temperature range of about 15° to 39° C. but other temperatures may also be utilized.

In yet another aspect of the present method, the high hexanal producing plant parts may be further admixed with other edible ingredients. Suitable ingredients are meals or flours other than soybean flour, and the like, as is known in the art and need not be listed herein. Other flours and food materials which can be admixed with the soybean flour with higher lipoxygenase 3 are products such as wheat meals or flours, particularly whole wheat flour, or other food ingredients such as cereals and pastries, meat and dairy products in which admixture with soybean flour is desirable with less problems with off-flavor development. This is by no means an all-encompassing list since other flours may also be utilized.

Typically, an amount of about 200 to 1300 units ($A_{235}$ $min^{-1}$ mg $protein^{-1}$) of lipoxygenase 3 enzyme are added per about 1 to 10 grams of hexanal-producing plant parts, e.g., soybean or soybean parts or flour. However, other proportions may also be utilized.

Also provided herein is a low odor soybean composition, which comprises
 a hexanal producing plant part meal or flour; and
 an agent comprising lipoxygenase 3 enzyme, which is optionally substantially devoid of lipoxygenase 1 and 2 enzyme activities, said lipoxygenase 3 enzyme being present in an amount sufficient to largely prevent the formation of hexanal by the meal or flour.

Particularly preferred whole soybean compositions such as soybean milk, soybean and enzyme-active soybean flour, and the like.

Soybean protein with active lipoxygenase 3 but essentially devoid of lipoxygenases 1 and 2 may be added to soybean meal, whole soybeans, and the like, prior to producing, e.g., soymilk, curds and the like, wheat germ and other high lipoxygenase and/or lipid material in accordance with this invention. A protein preparation having high lipoxygenase 3 but little or no lipoxygenase 1 or 2 activities may be readily prepared in an industrial scale, e.g., by using a one-step procedure as follows. A water extract of a meal prepared from seeds of a mutant line without lipoxygenase 2 is subjected to chromatofocusing or anion-exchange chromatography. By either method, the peak of lipoxygenase 3 activity may be easily separated from the lipoxygenase 1 activity. The fraction is then collected as is known in the art and utilized in the present invention. Such preparation may also be added to, e.g., wheat flour, or blended with other ingredients prior to baking bread, cake and/or pastry products. This addition would further enhance bleaching and the rheological properties of the dough used for the products.

In another embodiment, plant parts such as soybean seeds may be utilized which are produced by genetically altered plants. These genotypes possessing increased lipoxygenase 3 activity may be produced either by genetic engineering or by selective breeding by methods known in the art.

Particularly preferred are a soybean flour composition and a wheat germ composition. A preferred proportion of the enzyme to the meal or flour is about 1 to 500 units lipoxygenase 3 per g meal or flour, and more preferably about 10 to 200 units per g of meal or flour.

This composition may further comprise a flour other than soybean flour as described above. The preparation of high hexanal meal or flour to the other flour is about 2:100 to 1:1 by weight, and more preferably about 1:5 by weight.

Also provided herein is an edible product made from an odorless soybean composition which comprises a hexanal producing plant part meal or flour and an agent comprising lipoxygenase 3 enzyme, which is optionally substantially devoid of lipoxygenase 1 and 2 enzyme activities, said lipoxygenase 3 enzyme being present in an amount sufficient to significantly reduce the formation of hexanal by the meal or flour.

Part of this invention is also an edible product made from a low odor composition, which comprises a high hexanal producing plant flour, a flour other than soybean flour and an agent comprising lipoxygenase 3 enzyme which is optionally substantially devoid of lipoxygenases 1 and 2 activities.

The above edible products are typically breads, cake and pastry products, dairy and meat products. However, other products are also contemplated within the confines of this invention.

Also provided herein is a method of producing a plant meal or flour with improved flavor which comprises
 breaking up hexanal producing parts of a plant;
 adding thereto an agent comprising lipoxygenase 3 enzyme; and
 allowing the plant parts to remain in contact with the enzyme under conditions effective to attain the desired effect.

Typically, the different aspects of this method are similar to those described above as are the conditions for practicing each and every step of the method.

The preparation of purified lipoxygenase 3 enzyme is known in the art in general, but the procedure described herein in Example 2 below is particularly effective.

The above methods may also be practiced by substituting high lipoxygenase 3, low lipoxygenases 1 and 2—containing plant parts for the conventional plant parts and the lipoxygenase 3 agent.

Having now generally described this invention, the same will be better understood by reference to certain specific examples, which are included herein for purposes of illustration only and are not intended to be limiting of the invention or any embodiment thereof, unless those specified.

EXAMPLES

EXAMPLE 1

Hexanal production of soybean meal with lipoxygenase-producing mutant lines

The production of hexanal by aqueous homogenates of lyophilized, powdered meal from mature soybean seeds was investigated. Backcrossed mutant lines provided by Dr. Niels Nielsen (Davies and Nielsen (1987), supra)), and wild-type recurrent parent "Century" cell lines were utilized. The genotypes designated $lx_2lx_3$, $lx_1lx_3$, $lx_2$, $lx_3$ and $lx_1$ are lines which were backcrossed to the Century line and are homozygous recessive for the null (or very low) alleles of lipoxygenases 2 and 3 (only lipoxygenase 1 activity), lipoxygenases 1 and 3 (only lipoxygenase 2 activity), lipoxygenase 2 (only lipoxygenases 1 and 3 activities), lipoxygenase 3 (only lipoxygenases 1 and 2 activities) and lipoxygenase 1 (only lipoxygenases 2 and 3 activities), respectively.

Century seeds contain high levels of lipoxygenases 1, 2, and 3 as do all widely commercial soybean cultivars.

The present analyses were performed on seed harvested from plants grown concomitantly in a greenhouse with illumination supplemented to 13 hours/day with high intensity sodium halide lamps.

The soybean meal was prepared as follows. Seeds were lyophilized and ground to a fine powder in a standard coffee grinder. This material was stored in a moisture-tight container at 4° C. until used in the experiments.

Soybean meal samples were placed in 1.8 ml screw-top vials. To each vial was added 10 mg seed meal of one of the above genotypes, 50 μl 0.1 M sodium phosphate, pH 6.8 and 150 μl water containing 1 mM sodium linoleate and 15 μg cyclohexanone as an internal standard. All samples were stirred for 30 seconds and then incubated at 30° C. for 30 minutes. Thereafter 250 μl headspace vapor samples were analyzed by direct injection onto a 30 m×0.54 mm DB-5 (methylsilicone) fused silica GC column. The presence of hexanal was identified by mass spectrometry and co-chromatography on the DB-5 column.

The results are shown as ng hexanal per ml normalized to the cyclohexanone internal standard. Flame ionization detection was utilized for the measurements. The results are shown in FIG. 1 below. The error bars shown in the Figure represent the standard error of the mean values which were maximally 12.5% thereof.

EXAMPLE 2

Effect on hexanal yield of lipoxygenase 3 addition to soybean homogenates

The genotype designations and analytical procedures are the same as described in the legend to FIG. 1. Lipoxygenase 3 was added as 50 μl purified enzyme in 0.1 M sodium phosphate, pH 6.8 (750 deltaA$_{235}$ $_{nm}$ min$^{-1}$ μl$^{-1}$) in place of the 50 μl 0.1 M sodium phosphate, pH 6.8 blank for the control. The level of lipoxygenase 3 added is approximately the same as the endogenous level in wild-type seeds.

Lipoxygenase 3 was purified from the $lx_2$ line by the following procedure. Seed meal (1 g) was extracted on ice with 15 ml of 0.02 M sodium phosphate, pH 6.83 in a mortar and pestle, filtered through miracloth and centrifuged at 12,000 g for 10 minutes at 4° C. Calcium chloride (70 μM) was added to the supernatant which was then incubated for 30 minutes on ice. The preparation was then centrifuged as above and the resulting supernatant chromatographed on a Sephadex G-50 column (2.5×30 cm) using the same buffer as for extraction. The lipoxygenase peak was separated into lipoxygenases 1 and 3 on a PBE 94 chromatofocusing column (Pharmacia, Inc.) (2.5×30 cm) as described by Funk et al. (Funk, M. O., et al. Analyt. Biochem 146, 246–251 (1985).

Lipoxygenase 3 was further purified using a DEAE Sephadex A-50 column eluting with a linear gradient of 0.02 to 0.2 M sodium phosphate, pH 6.8 followed by gel filtration as above. The purified lipoxygenase 3 was concentrated using a Centricon 30 microconcentrator. This lipoxygenase 3 preparation gave only one band on native isoelectric focusing (IEF) (pH 4–7) and a band at 97 kD (the molecular weight for lipoxygenase 3) accounting for ca. 95% of the coomassie staining of sodium dodecylsulfate polyacrylamide electrophoresis (SDS-PAGE) gels (the other band was lower in MW and was immunodecorated with lipoxygenase 3 antibodies indicating that it was probably a lipoxygenase 3 degradation product).

The results obtained are shown in Table 1 below.

TABLE 1

| | Effect of Lipoxygenase 3 Enzyme on Hexanal Production of Soybean Homogenates. | | | |
|---|---|---|---|---|
| | ng hexanal/ml headspace ± SE of genotypes | | | |
| Treatment | $lx_2lx_3$ | $lx_1lx_3$ | $lx_3$ | Century |
| Control | 20.5 ± 0.5 | 28.2 ± 1.7 | 19.7 ± 1.7 | 1.80 ± 0.07 |
| LOX 3 | 1.20 ± 0.05 | 1.28 ± 0.07 | 1.62 ± 1.03 | 0.97 ± 0.15 |

EXAMPLE 3

Effect on hexanal production of addition of supplemental lipoxygenase 3 enzyme to soybean flour or meal The effect of the addition of lipoxygenase 3 enzyme to soybean flour was studied in accordance with the following protocol.

Figure 2:
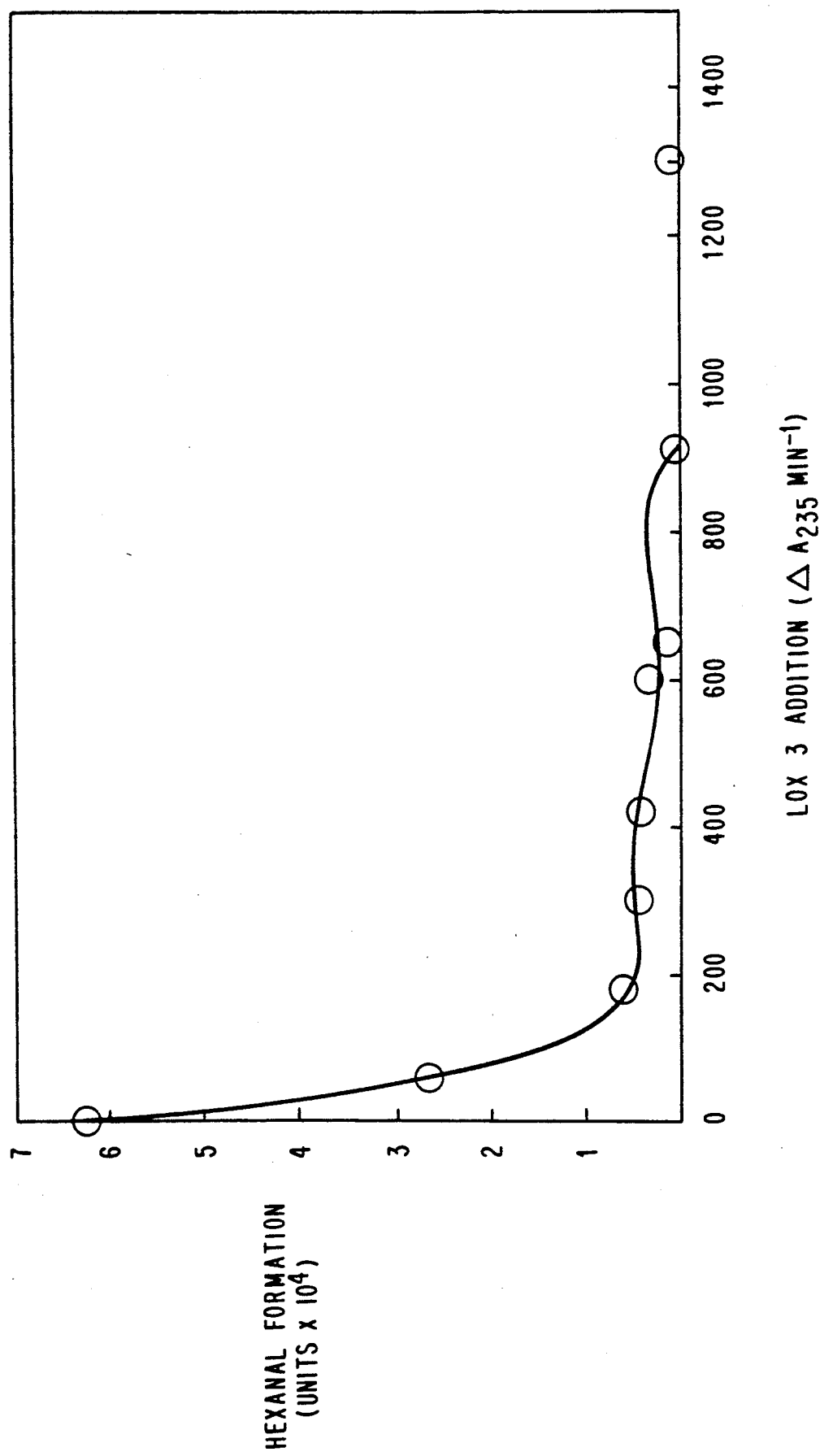
FIG. 2 shows hexanal production with the addition of various amounts of lipoxygenase 3 enzyme.
Figure 3:
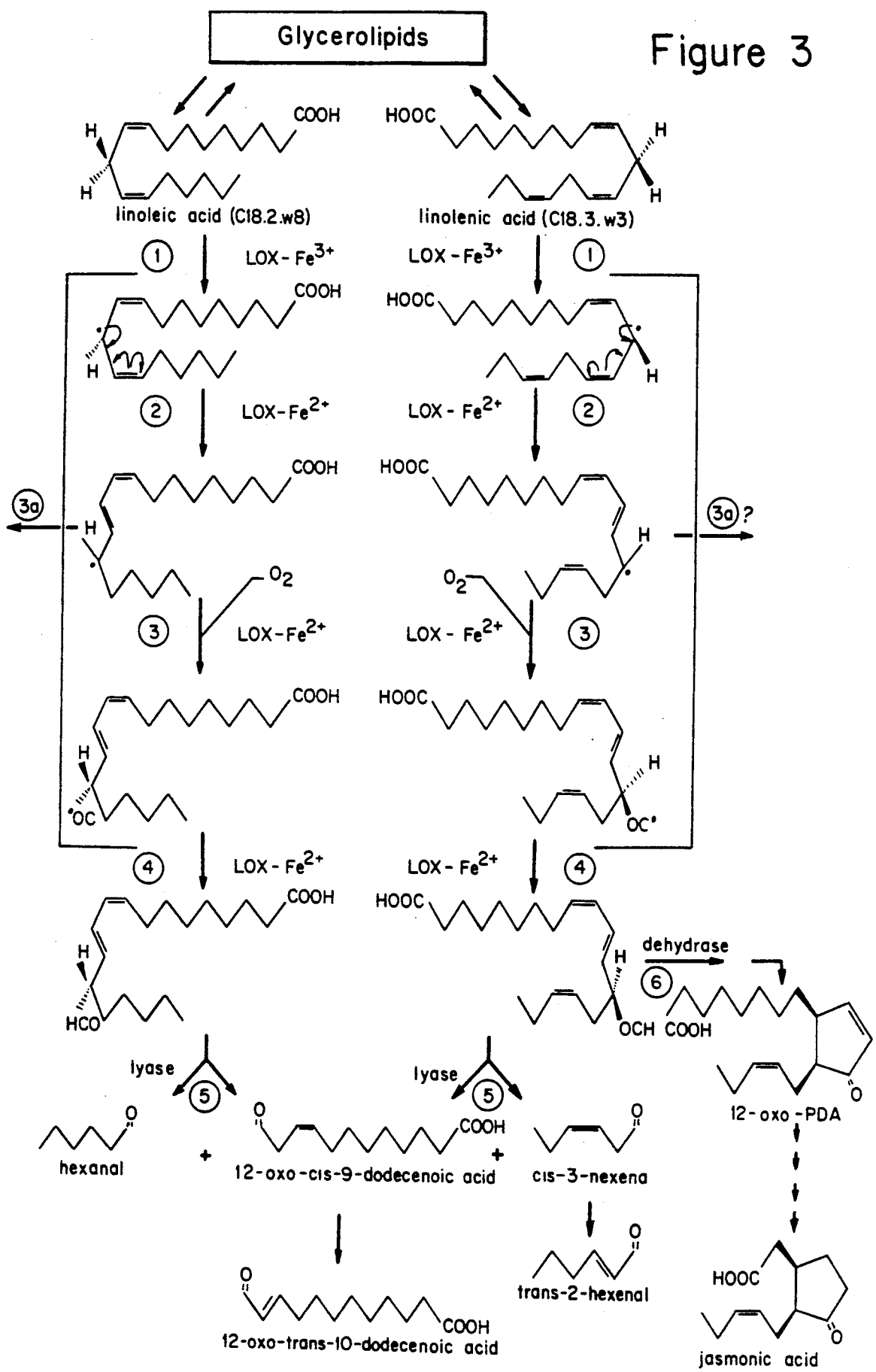
FIG. 3 shows a reaction scheme for the invention.

The production of hexanal by the samples was tested as shown above in Example 1. The results obtained indicate a progressive decrease in hexanal production which is dose dependent on the amount of enzyme added. Hexanal production is reduced up to 75 fold with high lipoxygenase 3 enzyme addition, e.g., amounts of enzyme greater than 900 deltaA$_{235}$ min$^{-1}$. These results can be seen in FIG. 2 accompanying this application.

EXAMPLE 4

Effect on hexanal production of addition of lipoxygenase 3 enzyme to ground wheat germ.

The effect of adding lipoxygenase 3 enzyme to ground wheat germ preparations was studied.

As in the case of Example 3 above, when lipoxygenase 3 enzyme is added to ground wheat germ a decrease in hexanal production is also observed. The results are shown in Table 2 below.

TABLE 2

Effect of Lipoxygenase 3 Enzyme Addition on Hexanal Production by Ground Wheat Germ.

| Sample | Hexanal Production (Area Units/mg flour) |
|---|---|
| Control | 1082 ± 305 |
| +Lipoxygenase 3 (50 μl) | 596 ± 267 |

The control sample contained the same components as the test sample except for the lipoxygenase 3 enzyme.
The test sample showed a 45% decrease in hexanal production.

A similar effect occurs in other high lipoxygenase and/or high lipid systems.

EXAMPLE 5

Effect on hexanal production of high lipoxygenase 3 levels in mixtures of soybean flour and whole wheat flour The effect of higher lipoxygenase 3 enzyme levels in mixtures containing soybean flour and whole wheat flour was studied according to the following protocol. Ten mg of these mixtures were added to screw-top vials and hexanal production was examined as described in Example 1 above.

In mixtures containing 20 wt % soybean flour and 80 wt % whole hard red winter wheat flour, a comparison of a control (no lipoxygenase 3 enzyme) and a test sample (normal lipoxygenase 3 enzyme levels present in soybean) evidenced a 6.84 fold decrease in hexanal levels.

This indicates that higher proportions of soybean flour can be added to whole wheat flour than was previously possible if lipoxygenase 3 enzyme is added to the soybean or if soybeans having high lipoxygenase 3 enzyme activity are utilized. With higher levels of lipoxygenase 3 enzyme in the mixture, increased amounts of soybean flour can be added to the mixture without reaching the adverse effects on its flavor which would be otherwise encountered.

EXAMPLE 6

Comparative effects on hexanal production of lipoxygenases 1, 2 and 3 enzymes

The addition of lipoxygenase enzyme active soybean flour to bread, cake and pastry products has been implicated in superior color and rheological characteristics such as texture and moisture content (Eskin et al., "Biochemistry of Lipoxygenase in Relation to Food Quality", Crit. Rev. Food Sci. Nutr. 9:1-40 (1977); Frazier, P. J., Baker's Digest 53: 8-29 (1979)).

The effect of the addition of lipoxygenase enzymes 1, 2, and 3 to whole wheat flour was studied using the protocol described in Example 1 above, but substituting whole wheat flour in place of soybean meal.

The results obtained indicate that the lipoxygenase 3 enzyme increases hexanal production in whole wheat flour to about the same degree as do lipoxygenases 1 and 2 enzymes per mg of protein. These results are shown in Table 3 below.

TABLE 3

Effects of Lipoxygenase Addition on Hexanal Production in Whole Wheat Flour System.

| Lipoxygenase | Activity per μl at pH Optimum | Hexanal Prod. (Fold Increase) | Fold Increase (per Activity Unit) |
|---|---|---|---|
| 1 | 460 | 3.02 | 0.0066 |
| 2 | 49 | 4.8 | 0.098 |
| 3 | 375 | 4.0 | 0.011 |

However, in addition to the above effect, the lipoxygenase 3 enzyme has a co-oxidation potential about two orders of magnitude greater than the lipoxygenase enzymes 1 or 2. These results are shown in Table 4 below.

TABLE 4

Carotenoid Co-oxidation Relative to Hexanal Production in Whole Wheat Flour.

| Lipoxygenase | Carotenoid Co-oxidation ($\mu l^{-1}$) | Carotenoid Co-oxidation (per Activity Unit) | Co-oxidation per Hexanal Increase |
|---|---|---|---|
| 1 | 1.68 | 0.0036 | 0.53 |
| 2 | 2.96 | 0.06 | 0.61 |
| 3 | 185.00 | 0.49 | 46.45 |

Accordingly, the lipoxygenase 3 enzyme has about 100 times the carotenoid co-oxidation potential relative to hexanal production when compared with lipoxygenase enzymes 1 and 2 (see, Table 4 above). The lipoxygenase 3 enzyme can therefore enhance the desirable properties of edible wheat products, as well as other plant products, with minimal detrimental effect on its flavor. These include lighter color, increased cross-linking of gluten, lightness of texture and higher moisture holding capacity.

The carotenoid co-oxidation values were obtained in accordance with the following protocol. Creatin (pyridine salt) was added to the standard linoleate substrate to 1 μM, which was then adjusted to pH 7.0. Wang and Hildebrand, "Effect of a Substituted Pyridazinone on the Decrease of Lipoxygenase Activity in Soybean Cotyledons", Plant Science 51: 29–36 (1987). The activity is presented as the change in $A_{446}$/min per mg protein. The activity using β-carotene as the substrate was similar.

The invention now being fully described, it will be apparent to one of ordinary skill in the art that many changes and modifications can be made thereto without departing from the spirit or scope of the invention as set forth herein.

We claim:

1. A method of reducing the formation of hexanal by plant parts, comprising
   breaking up hexanal producing parts of a plant;
   adding thereto an agent comprising lipoxygenase 3 enzyme; and
   allowing the plant parts to remain in contact with the enzyme under conditions effective to attain a reduction of hexanal content in the plant parts.

2. The method of claim 1, wherein
   the plant parts are selected from the group consisting of soybeans, wheat germ, mixtures thereof and mixtures thereof with other edible products.

3. The method of claim 1, wherein
   the plant parts are broken up into a meal or flour.

4. The method of claim 1, wherein the enzyme agent substantially lacks lipoxygenase 1 and 2 enzyme activities.

5. The method of claim 1, further comprising
admixing the plant parts with other edible ingredients.

6. The method of claim 5, wherein
the other edible ingredients are selected from the group consisting of a meal or flour other than soybean flour and wheat germ.

7. A method of reducing the formation of hexanal by plant parts, comprising
breaking up hexanal producing parts of a plant where the plant parts are mutant lipoxygenase 3 enzyme-producing parts substantially lacking lipoxygenase 1 and 2 enzymes activities; and
allowing the plant parts to remain in contact with the enzyme under conditions effective to attain a reduction of hexanal content in the plant parts.

8. A low odor plant part composition, comprising
a hexanal producing plant part; and
an agent comprising lipoxygenase 3 enzyme substantially devoid of lipoxygenase 1 and 2 activities, said lipoxygenase 3 enzyme being present in an amount sufficient to substantially reduce the formation of hexanal by the plant parts.

9. The composition of claim 8, wherein
the plant part is selected from the group consisting of
soybean milk;
soybean curd; and
enzyme-active soybean flour.

10. The low odor composition of claim 8, further comprising
a meal or flour composition other than soybean meal or flour and wheat germ.

11. The low odor composition of claim 10 obtained by a method comprising
breaking up the plant parts, adding thereto an agent comprising lipoxygenase 3 enzyme and allowing the plant parts to remain in contact with the enzyme under conditions effective to attain a reduction of hexanal content in the plant parts.

12. An edible product comprising the low odor composition of claim 8.

13. An edible product comprising the low odor composition of claim 10.

14. A method of producing low odor plant parts, comprising
breaking up hexanal producing parts of a plant;
adding thereto an agent comprising lipoxygenase 3 enzyme; and
allowing the plant parts to remain in contact with the enzyme under conditions effective to attain a reduction of hexanal content in the plant parts.

15. The method of claim 14, wherein
the plant parts are selected from the group consisting of soybeans, wheat germ, mixtures thereof and mixtures thereof with other edible products.

16. A method of producing a low odor meal or flour, comprising
the method of claim 14; and
breaking up the plant parts into a meal or flour.

17. The method of claim 14, wherein
the enzyme agent substantially lacks lipoxygenase 1 and 2 enzyme activities.

18. The method of claim 14, further comprising
admixing the plant parts with other edible ingredients.

19. The method of claim 18, wherein
the other edible ingredients are selected from the group consisting of meals and flours other than soybean flour and wheat germ.

20. A product obtained by the method of claim 14.

* * * * *